United States Patent [19]

Finch et al.

[11] Patent Number: 4,801,735

[45] Date of Patent: Jan. 31, 1989

[54] PHARMACEUTICAL COMPOUNDS

[75] Inventors: Mark A. W. Finch, Basingstoke; John R. Harris, Guildford, both of England

[73] Assignee: Lilly Industries Limited, London, England

[21] Appl. No.: 801,524

[22] Filed: Nov. 25, 1985

[30] Foreign Application Priority Data

Nov. 28, 1984 [GB] United Kingdom ............... 8430072

[51] Int. Cl.$^4$ ...................... C07C 69/76; C07C 65/01
[52] U.S. Cl. .................................... 560/75; 562/478; 564/170; 564/265; 564/389; 568/442; 568/766; 544/176; 548/530; 546/226
[58] Field of Search ........................... 560/75; 562/478; 564/170, 265, 389; 568/442, 766; 544/176; 548/530; 546/226; 514/562, 617, 640, 649, 678, 699

[56] References Cited

U.S. PATENT DOCUMENTS 3,236,898  2/1966  Green et al. ..................... 260/600
3,998,851  12/1976  Reidenbacher ..................... 549/290

OTHER PUBLICATIONS

Tetrahedron Letters, 22(51) 5221-4, 1981.
Tetrahedron Letters, 21 pp. 3423-3426, 1980.
Hamasaki et al., Agric. Biol. Chem., 45(1), 313 (1981).
Hamasaki et al., Agric. Biol. Chem., 44(7), 1685 (1980).
Bohlmann et al., Chem. Berichte, 112(7), 2394 (1979).
Schill et al., Chem. Berichte, 108(5), 1570 (1975).
Manecke et al., Chem. Berichte, 96(7), 2013 (1963).
Murakami et al., Chem. Pharm. Bull., 15(11), 1817 (1967).
Hung et al., Eur. J. Med. Chem.-Chim. Ther., 18(1), 61 (1983).
Barton et al., J. Chem. Soc. C, 12, 2231 (1971).
Falshaw et al., J. Chem. Soc. Chem. Commun., 14, 491 (1973).
L. M. Harwood, J. Chem. Soc., Perkin Trans., 1(11), 2577 (1984).
Green et al., J. Chem. Soc., Perkin Trans., 1(10), 2389 (1984).
Giles et al., J. Chem. Soc., Perkin Trans., 1(9), 2147 (1983).
Bruce et al., J. Chem. Soc., Perkin Trans., 1(10), 2677 (1981).
Bruce et al., J. Chem. Soc., Perkins Trans., 1(2), 288 (1974).
Bruce et al., J. Chem. Soc., Perkin Trans., 1(3), 372 (1972).
Shah et al., J. Indian Chem. Soc., 52(5), 436 (1975).
Glennon et al., J. Med. Chem., 23(3), 294 (1980).
Nair et al., Phytochemistry, 16(3), 390 (1977).
M. Lounasmaa, Soumen Kemistilehti, A., 41(2), 24 (1968).
Casiraghi et al., Synthesis, 2, 124 (1980).
Nair et al., Tetrahedron Lett., 35, 3233 (1979).
Erdtman et al., Tetrahedron Lett., 38, 3389 (1970).
Irie et al., Yakugaku Zasshi, 88(5), 627 (1968).
Chemical Abstracts, 101:69659t.
Chemical Abstracts, 101:69660m.
Chemical Abstracts, 96:179433a.
Chemical Abstracts, 96:122636q.
Chemical Abstracts, 95:24321t.
Chemical Abstracts, 85:142813w.
Chemical Abstracts, 78:33840n.
Chemical Abstracts, 68:112174v.
Chemical Abstracts, 68:109814y.
Chemical Abstracts, 56:4646h.
Chemical Abstracts, 56:4646i.
Chemical Abstracts, 56:4647a.
Chemical Abstracts, 56:4647b.
Chemical Abstracts, 56:4647c.

Primary Examiner—Paul J. Killos
Attorney, Agent, or Firm—Robert A. Conrad; Leroy Whitaker

[57] ABSTRACT

Compounds are described of the following formula

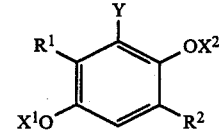

in which $R^1$ and $R^2$ are each hydrogen, $C_{1-12}$ alkyl or $C_{2-12}$ alkenyl, at least one of $R^1$ and $R^2$ being $C_{1-12}$ alkyl or $C_{2-12}$ alkenyl; $X^1$ and $X^2$ are each hydrogen or a protecting group; and Y is (a) —(CH=CH)$_n$Z in which n is 1, 2 or 3 and Z is —CHO, —CH$_2$OH, —COR$^3$, —(CH$_2$)$_m$—COR$^3$ or —(CH$_2$)$_p$CH=CH(CH$_2$)$_q$—COR$^3$ in which m is an integer of 1 to 12, p is an integer of 1 to 4, q is an integer of 1 to 10 and $R^3$ is (i) —OH or (ii) —NR$^4$R$^5$ where $R^4$ and $R^5$ are each hydrogen, $C_{1-4}$ alkyl or optionally substituted phenyl, or $R^4$ and $R^5$ together with the nitrogen atom to which they are attached form a morpholino, pyrrolidinyl or piperidino ring, (b) —CH=NR$^6$ in which $R^6$ is (i) —OH, (ii) $C_{1-12}$ alkyl optionally substituted by —OH, —COOH or —NR$^7$R$^8$ where $R^7$ and $R^8$ are each hydrogen or $C_{1-4}$ alkyl, (iii) optionally substituted phenyl or (iv) —NR$^9$R$^{10}$ in which $R^9$ is hydrogen and $R^{10}$ is optionally substituted phenyl or $C_{1-4}$ alkyl CO—, or in which $R^9$ and $R^{10}$ together with the nitrogen atom to which they are attached form a morpholino, pyrrolidinyl or piperidino ring, (c) —CH$_2$NHR$^{11}$ in which $R^{11}$ is $C_{1-12}$ alkyl optionally substituted with hydroxy or carboxy or optionally substituted phenyl, or (d) —CHOHR$^{12}$ or

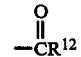

in which $R^{12}$ is hydrogen or $C_{1-12}$ alkyl;

and lactones, salts and esters thereof; provided that when one of $R^1$ and $R^2$ is hydrogen and the other is $C_{1-12}$ alkyl, Y is —(CH=CH)$_n$Z, n is 1 and Z is —COOH only salts are included.

The compounds have pharmaceutical activity.

5 Claims, No Drawings

PHARMACEUTICAL COMPOUNDS

This invention relates to novel compounds, pharmaceutical compositions containing them and their use as pharmaceuticals.

The compounds of the invention have the formula

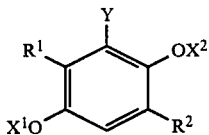

(I)

in which $R^1$ and $R^2$ are each hydrogen, $C_{1-12}$ alkyl or $C_{2-12}$ alkenyl, at least one of $R^1$ and $R^2$ being $C_{1-12}$ alkyl or $C_{2-12}$ alkenyl; $X^1$ and $X^2$ are each hydrogen or a protecting group; and Y is (a) $-(CH=CH)_nZ$ in which n is 1, 2 or 3 and Z is $-CHO$, $-CH_2OH$, $-COR^3$, $-(CH_2)_m-COR^3$ or $-(CH_2)_pCH=CH(CH_2)_q-COR^3$ in which m is an integer of 1 to 12, p is an integer of 1 to 4, q is an integer of 1 to 10 and $R^3$ is (i) $-OH$ or (ii) $-NR^4R^5$ where $R^4$ and $R^5$ are each hydrogen, $C_{1-4}$ alkyl or optionally substituted phenyl, or $R^4$ and $R^5$ together with the nitrogen atom to which they are attached form a morpholino, pyrrolidinyl or piperidino ring, (b) $-CH=NR^6$ in which $R^6$ is (i) $-OH$, (ii) $C_{1-12}$ alkyl optionally substituted by $-OH$, $-COOH$ or $-NR^7R^8$ where $R^7$ and $R^8$ are each hydrogen or $C_{1-4}$ alkyl, (iii) optionally substituted phenyl or (iv) $-NR^9R^{10}$ in which $R^9$ is hydrogen and $R^{10}$ is optionally substituted phenyl or $C_{1-4}$ alkylCO—, or in which $R^9$ and $R^{10}$ together with the nitrogen atom to which they are attached form a morpholino, pyrrolidinyl or piperidino ring, (c) $-CH_2NHR^{11}$ in which $R^{11}$ is $C_{1-12}$ alkyl optionally substituted with hydroxy or carboxy or optionally substituted phenyl, or (d) $-CHOHR^{12}$ or

in which $R^{12}$ is hydrogen or $C_{1-12}$ alkyl;
and lactones, salts and esters thereof; provided that when one of $R^1$ and $R^2$ is hydrogen and the other is $C_{1-12}$ alkyl, Y is $-(CH=CH)_nZ$, n is 1 and Z is $-COOH$ only salts are included.

Compounds of formula (I) when in unprotected form ($X^1$ and $X^2$ are both hydrogen) are inhibitors of leukotriene synthesis and are indicated for use in a variety of pharmacological conditions.

In the above formula (I) reference to an alkyl group includes, for example, methyl, ethyl, propyl, isopropyl, tertiary butyl and groups containing up to twelve carbon atoms, which may be straight or branched chain. When $R^1$ or $R^2$ is alkyl it preferably contains from 3 to 7 carbon atoms.

Similarly an alkenyl group contains up to twelve carbon atoms and can be straight or branched. An alkenyl group is preferably of the formula: $R^{13}(CH=CHCH_2)_r-$ where $R^{13}$ is hydrogen or $C_{1-8}$ alkyl and r is 1 to 3, preferred examples being $C_5H_{11}(CH=CHCH_2)_2$ and allyl.

When $X^1$ and $X^2$ are protecting groups they can be any suitable group that protects the hydroxyl substituent during preparative reactions and such groups are well known in the art. Examples include the tetrahydropyran or silyl protecting groups and an especially useful example is the methylmethylether group formed, for example, by reacting a free hydroxyl with chloromethylmethylether. Such groups can be readily displaced by acid to give compounds with the free hydroxyl when desired.

When one of the groups such as $R^4$, $R^5$ or $R^{10}$ is optionally substituted phenyl, it is preferably phenyl optionally substituted with hydroxyl, halo especially fluoro, chloro or bromo, $C_{1-14}$ alkyl especially methyl or ethyl, $C_{1-4}$ alkoxy especially methoxy or ethoxy, nitro and carboxy. When the phenyl ring is substituted there are generally 1 to 3 substituents and the most preferred are $C_{1-4}$ alkyl, halo or hydroxy.

It is preferred that $R^1$ and $R^2$ are $C_{1-12}$ alkyl or $C_{2-12}$ alkenyl, and the most preferred compounds are those in which both $R^1$ and $R^2$ are $C_{1-12}$ alkyl or $C_{2-12}$ alkenyl. Preferably an alkyl group is $C_{2-12}$ alkyl. The group Y is preferably of the formula $-(CH=CH)_nZ$. When Z is $-CHO$, $-CH_2OH$ or $-COR^3$ the preferred value of n is 2, and when Z is $-(CH_2)_m-COR^3$ or $-(CH_2)_pCH=CH(CH_2)_q-COR^3$, n is preferably 1, and the values m and q are both preferably an integer of 1 to 4. Z is most preferably $-COR^3$ and especially $-COOH$ and esters derived from the carboxy group.

The compounds of the invention include salts and these can be any of the well known base addition salts that form salts at a carboxyl group such as for example with those compounds in which Z is $-COOH$. Examples of such salts are those derived from ammonium hydroxide and alkali and alkaline earth metal hydroxides, carbonates and bicarbonates, as well as salts derived from aliphatic and aromatic amines and aliphatic diamines. Bases especially useful in the preparation of such salts include ammonium hydroxide, potassium carbonate, sodium bicarbonate, calcium hydroxide, methylamine, diethylamine, ethylene diamine and cyclohexylamine. The potassium and sodium salt forms are particularly preferred.

Also included in the invention are esters of the compounds of formula (I), principally those formed with compounds in which Z is $-COOH$. These can be any of the well known ester groups suitable for forming such derivatives. Preferred esters are those derived from and alcohol or an aminoalcohol. In such instances Z has the value $-COOR^{14}$ where $R^{14}$ is $C_{1-12}$ alkyl or $-(CH_2)_sNR^{15}R^{16}$ where $R^{15}$ and $R^{16}$ are each hydrogen or $C_{1-4}$ alkyl, especially methyl or ethyl, and s is 1, 2 or 3. The preferred esters are those derived from methanol and ethanol, that is, the methyl and ethyl esters of the compounds of formula (I).

Apart from pharmaceutically acceptable addition salts and esters, other salts and esters are also included within the scope of the invention since they may serve as intermediates in the purification of compounds or in the preparation of other pharmaceutically acceptable derivatives, or they may be useful for identification, characterisation or purification of the free compound.

A preferred group of compounds of formula (I) is of the following formula

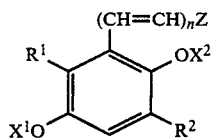

in which $R^1$ and $R^2$ are each hydrogen, $C_{1-12}$ alkyl or $C_{2-12}$ alkenyl, at least one of $R^1$ and $R^2$ being $C_{1-12}$ alkyl or $C_{2-12}$ alkenyl, $X^1$ and $X^2$ are each hydrogen or a protecting group, n is 1, 2 or 3, and Z is —$COR^3$ in which $R^3$ is (i) —OH, (ii) —$OR^{14}$ where $R^{14}$ is $C_{1-12}$ alkyl or —$(CH_2)_sNR^{15}R^{16}$ where $R^{15}$ and $R^{16}$ are each hydrogen or $C_{1-4}$ alkyl and s is 1, 2 or 3, or (iii) —$NR^4R^5$ where $R^4$ and $R^5$ are each hydrogen, $C_{1-4}$ alkyl or phenyl optionally substituted by halogen or $C_{1-4}$ alkyl, or $R^4$ and $R^5$ together with the nitrogen atom to which they are attached form a morpholino, pyrrolidinyl or piperidino ring, provided that when one of $R^1$ and $R^2$ is hydrogen and the other is $C_{1-12}$ alkyl, n is 1 and Z is —$COR^3$, $R^3$ is —OH or —$NR^4R^5$; and salts thereof. Of these compounds a preferred group is one in which $R^1$ and $R^2$ are both $C_{1-12}$ alkyl or $C_{2-12}$ alkenyl.

A further preferred group of compounds of formula (I) is of the following formula

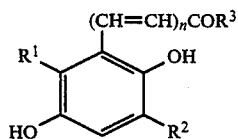

in which $R^1$ and $R^2$ are each $C_{3-7}$ alkyl or $R^{13}(CH=CHCH_2)_r$— where $R^{13}$ is hydrogen or $C_{1-8}$ alkyl and r is 1 to 3, and $R^3$ is —OH, —$OR^{14}$ where $R^{14}$ is $C_{1-4}$ alkyl or —$(CH_2)_2NR^{15}R^{16}$ where $R^{15}$ and $R^{16}$ are each hydrogen or $C_{1-4}$ alkyl, or —$NR^4R^5$ where $R^4$ and $R^5$ are each hydrogen, $C_{1-4}$ alkyl or phenyl optionally substituted by halogen or $C_{1-4}$ alkyl; and salts thereof. Of these compounds those of the following formula are most preferred

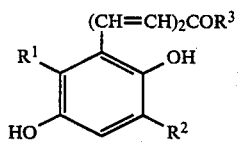

in which $R^1$ and $R^2$ are both allyl or propyl, and $R^3$ is —OH or —$OR^{14}$ where $R^{14}$ is $C_{1-4}$ alkyl; and salts thereof.

It will be appreciated that when Y is —$(CH=CH)_nZ$ the compounds of formula (I) exist in stereoisomeric (Z and E) forms about the C—C double bonds and such forms are included in the present invention, the E forms being preferred. Also it will be appreciated that compounds in which Z is —COOH and $X^2$ is hydrogen can form internal lactones of the formula

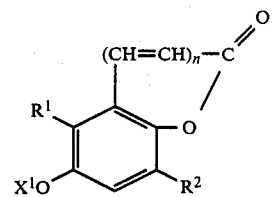

and such compounds are included within the scope of formula (I) above.

The invention also includes a process for preparing compounds of formula (I) which comprises (a) heating a compound of formula

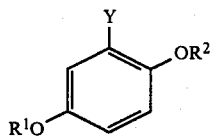

in which Y has the values given above and $R^1$ and $R^2$ are $C_{1-12}$ alkenyl, to provide a compound of formula (I) in which $R^1$ and $R^2$ are $C_{1-12}$ alkenyl and $X^1$ and $X^2$ are hydrogen, or (b) reacting a compound of the formula

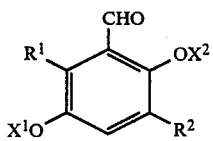

(i) under Wittig or Knoevenagel conditions to provide a compound of formula (I) in which Y is —$(CH=CH)_nZ$, (ii) with hydroxylamine to provide a compound of formula (I) in which Y is —CH=NOH, (iii) with an amine of formula $H_2NR^6$ in which $R^6$ is $C_{1-12}$ alkyl optionally substituted by —OH, —COOH or —$NR^7R^8$ where $R^7$ and $R^8$ are each hydrogen or $C_{1-4}$ alkyl, optionally substituted phenyl, or —$NR^9R^{10}$ where $R^9$ is hydrogen and $R^{10}$ is optionally substituted phenyl or $C_{1-4}$ alkylCO—, or in which $R^9$ and $R^{10}$ together with the nitrogen atom to which they are attached form a morpholino, pyrrolidinyl or piperidino ring, to provide a compound of formula (I) in which Y is —$CH=NR^6$, or (iv) with a Grignard or alkyl lithium reagent of the formula $R^{12}M$ in which M is MgBr or lithium and $R^{12}$ is $C_{1-12}$ alkyl, to provide a compound of formula (I) in which Y is —$CHOHR^{12}$ optionally followed by oxidation;

optionally followed by reduction to provide a compound in which $R^1$ and $R^2$ is $C_{1-12}$ alkyl, or Y is —$(CH=CH)_nCHO$, —$(CH=CH)_nCH_2OH$ or —$CH_2NHR^{11}$, or by conversion of one Z group to another, or by removal of a protecting group.

The principal route for the preparation of the compounds is by the rearrangement of a compound of formula (II) above, preferably by heating the compound to a temperature of from 100° C. to 250° C. in an inert organic solvent such as for example nitrobenzene to effect the introduction of alkenyl substituent or substituents in the phenyl ring. The products of the rearrangement, namely, the compounds of formula (I) in which $R^1$ and $R^2$ are alkenyl can then optionally be reduced to give the corresponding compounds in which $R^1$ and $R^2$ are alkyl.

Compounds of formula (II) can be prepared by reacting a derivative of formula

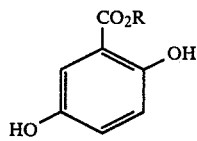 (IV)

where R is $C_{1-4}$ alkyl, with a compound of formula $R^1X$ or $R^2X$, $R^1$ and $R^2$ being alkenyl groups, and X a leaving group such as for example halogen, in the presence of a base, at a temperature of from 50° C. to 70° C. and in an inert organic solvent, followed by reduction to the aldehyde. The aldehyde can then be converted to the appropriate value of side chain Y by one of the methods (b)(i), (ii), (iii) or (iv) defined above, namely, by reaction with Wittig or Knoevenagel reagent, with hydroxylamine, with amine of formula $H_2NR^6$, or with Grignard or alkyl lithium reagent.

The above compound of formula (IV) can be reduced to the aldehyde by, for example, reaction with di-isobutyl aluminium hydride followed by a Collins oxidation, and the aldehyde reacted with Wittig or Knoevenagel reagent to form the appropriate ester. For example, reaction of a compound of formula

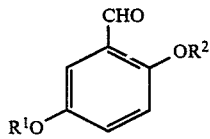 (V)

with a Wittig reactant of formula $Ph_3P=CH-CO_2Me$, $Ph_3P=CH-CH=CH-CO_2Me$ or

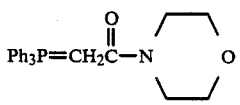

gives, respectively, compounds of the formulae:

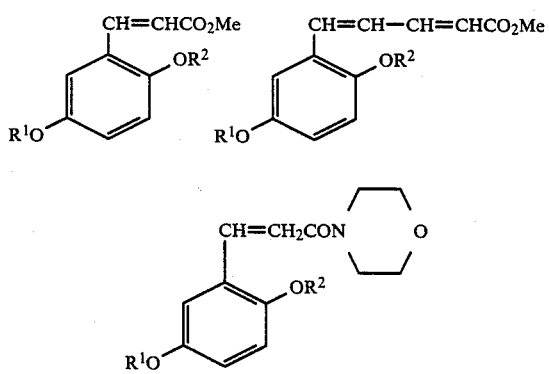

Expressed more generally, the Wittig reagent employed is of the formula

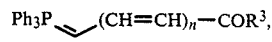

where n is 0, 1 or 2, $Ph_3PCH_2(CH_2)_mCOR^3$ or $Ph_3PCH_2(CH_2)_pCH=CH(CH_2)_q-COR^3$, in which $R^3$ is $-OC_{1-12}$ alkyl or $-NR^4R^5$ or

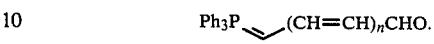

The reaction is generally carried out at a temperature of from 0° C. to 150° C. in an inert organic solvent.

Alternatively, the unsaturated side chain can be introduced into the molecule by reaction of the appropriate aldehyde with $CH_2(COOH)_2$ according to the reaction scheme:

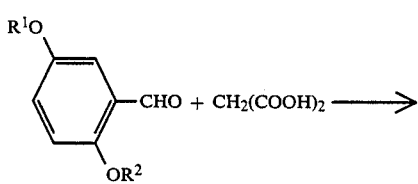

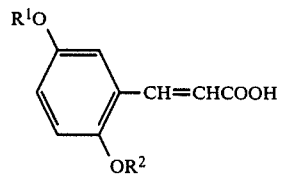

In order to obtain compounds in which n in formula (I) is 2 or 3, a carboxyl derivative may be reduced to the corresponding aldehyde by conventional chemical reduction, and the condensation reaction repeated. The Knoevenagel reaction can be carried out in an organic solvent for example pyridine, at a temperature of from 0° C. to 150° C.

When it is desired to prepare the starting materials of formula (II) in which Y is $-CH=NOH$, the appropriate aldehyde of formula (V) is reacted with excess hydroxylamine at a temperature of, for example, from 0° C. to 100° C. in an inert solvent such as for example a mixture of water and ethanol.

When it is desired to prepare the starting materials of formula (II) in which Y is $-CH=NR^6$, $R^6$ being other than $-OH$, the appropriate amine is reacted with an aldehyde of formula (V) in an organic solvent such as for example toluene or benzene at reflux temperature and in the presence of an acid catalyst such as for example p-toluene sulphonic acid. A Dean and Stark apparatus can be used for this purpose, and the reaction leads to loss of water and formation of the required imine or hydrazone.

When it is desired to prepare the starting materials of formula (II) in which Y is $-CHOHR^{12}$ the aldehyde of formula (V) is reacted with a Grignard reagent or alkyl lithium in an organic solvent such as for example tetrahydrofuran at a temperature of, for example, from $-70°$ C. to 20° C. The appropriate Grignard reagents and alkyl lithium derivatives are well known in the art. If it is desired to prepare a compound in which Y is

the alcohol product of the above reaction can be oxidised using the Collins reaction.

It will be appreciated that the reactions described above can be carried out on a compound of formula

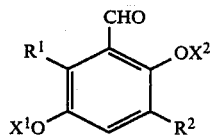

(III)

derived by rearrangement of the compound of formula (V) above and protection of the free hydroxyl groups if the subsequent reaction so requires.

Thus the Wittig and Knoevenagel reactions described above can be performed on the "rearranged" aldehyde, for example, a reaction:

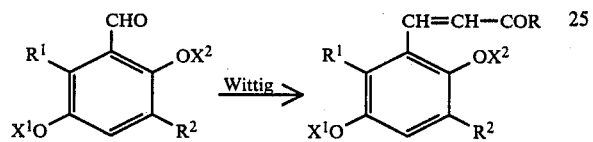

followed by optional removal of protecting groups. Reactions with hydroxylamine, with amine of formula $H_2NR^6$ and the Grignard and alkyl lithium reactions described above, process step (b) (ii), (iii) and (iv), can be utilised in this route for preparing the compounds of the invention. The reaction conditions are the same as those described above in relation to process step (a).

Compounds prepared by the above routes can be reduced to provide the derivatives in which $R^1$ or $R^2$ is $C_{2-12}$ alkyl or is $-(CH=CH)_nCHO$, $-(CH=CH)_nC$-$H_2OH$ or $-CH_2NHR^{11}$. The reduction process can be carried out by a chemical reaction method to prepare $-(CH=CH)_nCHO$ or $-(CH=CH)_nCH_2OH$, or by hydrogenating the double bond to prepare an alkyl group or $-CH_2NHR^{11}$ by for example use of hydrogen and palladium on charcoal, or platinum on carbon, at a temperature of for example from 0° C. to 80° C. such as from 20° C. to 25° C.

It will be appreciated that compounds of formula (I) in which Z takes various values can often be readily interconverted by well known methods. For example when Z is carboxyl other derivatives, such as esters, amides and salts may be prepared by methods well known in the art. For instance derivatives can be prepared by reacting a compound of formula

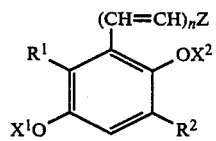

in which $R^1$ and $R^2$ have the values given above, $X^1$ and $X^2$ are protecting groups and Z is —COOH or —COCl, with an alcohol of the formula $R^{14}OH$ where $R^{14}$ is $C_{1-12}$ alkyl or —$(CH_2)_sNR^{15}R^{16}$ where s and $R^{15}$ and $R^{16}$ are as defined above, or with an amine of formula $HNR^4R^5$ where $R^4$ and $R^5$ are as defined above.

An example of the preparation of a preferred group of compounds of the invention is illustrated in the following reaction scheme:

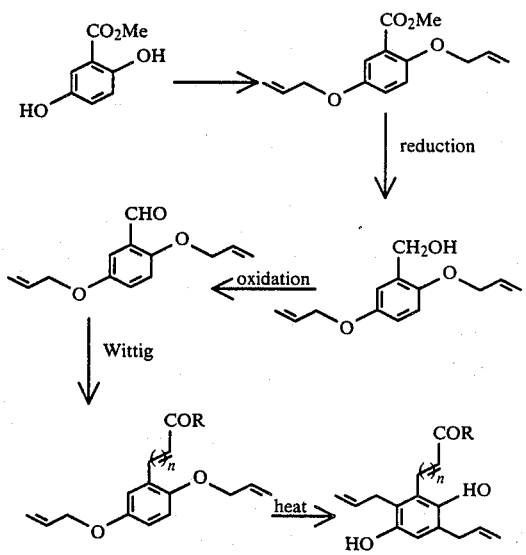

The compounds of the present invention are pharmacologically active, being inhibitors of leukotriene formation as shown by their action in the ionophore lipoxygenase test described by Harvey and Osborne, Journal of Pharmacological Methods 9, 147–155 (1983). Elicited guinea pig peritoneal cells are preincubated with the test compound and challenged with a calcium ionophore in the presence of $^{14}C$ arachidonic acid. The radiolabelled metabolites are extracted and separated by thin layer chromatography and the lipoxygenase products analysed by quantitative radiochromatogram scanning. In this test, the compounds of the invention described in the following Examples are active at concentrations of 30 micromolar or less. The compounds are also active in the "guinea-pig chopped lung test" described by Mongar and Schild in the Journal of Physiology (London) (3) 207 (1956), or by Brocklehurst, Journal of Physiology (London) 152, 414 (1960) at dosages of less than 30 micromolar.

The compounds are accordingly indicated for therapeutic use in the treatment of diseases in which leukotrienes are implicated. These include immediate hypersensitivity diseases, allergic reactions of the pulmonary system in which leukotrienes are thought to be causal mediators of bronchospasm, for example, in allergic lung disorders such as extrinsic asthma and industrial asthmas such as Farmers lung and Pigeon Fanciers lung, and in other inflammatory disorders, for example, associated with acute or chronic infectious diseases such as allergic skin diseases, ectopic and atopic eczemas, psoriasis, contact hypersensitivity and angioneurotic oedema, bronchitis and cystic fibrosis and rheumatic fever. Furthermore, owing to their inhibition of leukotriene formation, the compounds have potential activity against a wide range of inflammatory diseases, and are also indicated for use in cancer treatment.

The compounds may be administered by various routes, for example, by the oral or rectal route, by inhalation, topically or parenterally, for example by injection, being usually employed in the form of a pharmaceutical composition. Such compositions form part of the present invention and are prepared in a manner well known in the pharmaceutical art and normally comprise at least one active compound in association with a pharmaceutically acceptable diluent or carrier. In making the compositions of the present invention, the active ingredient will usually be mixed with a carrier, or diluted by a carrier, or enclosed within a carrier which may, for example, be in the form of a capsule, sachet, paper or other container. Where the carrier serves a diluent, it may be a solid, semi-solid, or liquid material which acts as a vehicle, excipient or medium for the active ingredient. Thus, the composition may be in the form of tablets, lozenges, sachets, cachets, elixirs, suspensions, aerosols as a solid or in a liquid medium, ointments containing for example up to 10% by weight of the active compound, soft and hard gelatin capsules, suppositories, injection solutions and suspensions and sterile packaged powders. For administration by inhalation, particular forms of presentation include aerosols, atomisers and vaporisers.

Some examples of suitable carriers are lactose, dextrose, sucrose, sorbitol, mannitol, starches, gum acacia, calcium phosphate, alginates, tragacanth, gelatin, syrup, methyl cellulose, methyl- aned propyl-hydroxybenzoate, talc, magnesium stearate and mineral oil. The compositions of the invention may, as is well known in the art, be formulated so as to provide quick, sustained or delayed release of the active ingredient after administration to the patient.

Where the compositions are formulated in unit dosage form, it is preferred that each unit dosage form contains from 5 mg to 500 mg, more usually 25 to 200 mg, of the active ingredient. The term "unit dosage form" refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and for example dosages per day will normally fall within the range of 0.5 to 300 mg/kg and in the treatment of adult humans, more usually in the range of from 5 to 100 mg/kg. However it will be understood that the amount of the compound actually administered will be determined by a physician, in the light of the relevant circumstances including the condition to be treated, the choice of compound to be administered and the chosen route of administration and therefore the above dosage ranges are not intended to limit the scope of the invention in any way.

The following Examples illustrate the invention. The structure of the compounds prepared was confirmed by I.R. and/or n.m.r. and/or mass spectra and the purity of the product was checked in most cases by HPLC. The involatile products were examined by mass spectrometry using the fast atom bombardment (FAB) technique in the negative ion mode. Significant [M-H]$^-$ ions (and characteristic fragment ions) were observed.

EXAMPLE 1

Methyl-2,5-dihydroxybenzoate 2,5-Dihydroxybenzoic acid (30 g) was added to methanol (100 ml) which had been acidified with hydrogen chloride gas. The solution was refluxed for 12 hours when the solvent was removed. The resulting solid was taken up in diethyl ether (200 ml) and washed with water (2×100 ml). The organic layer was dried over magnesium sulphate and the solvent removed under vacuum. The resulting solid (30 g) (m.p. 83°–84° C.) was identified as the desired methyl ester.

EXAMPLE 2

Methyl-2,5-di-O-allylbenzoate

To a solution of the methyl-2,5-dihydroxybenzoate (10 g) in acetone (120 ml) was added potassium carbonate (20.5 g) and allyl bromide (15.5 g). The mixture was refluxed for 3 hours when the solvent was removed under vacuum. The resulting solid was taken up in diethyl ether (250 ml) and washed with water (2×150 ml). The organic layer was dried over magnesium sulphate and removed under vacuum to yield the desired O-allylated product (13.5 g) as an oil.

EXAMPLE 3

2,5-Di-O-allylbenzyl alcohol

To a stirred solution of the methy ester (13.5 g) in dichloromethane (150 ml), at 0° C. and under an atmosphere of nitrogen was slowly added a solution of diisobutyl-aluminium hydride (46 g, 20% in toluene). The reaction was quenched after 30 minutes by the slow, dropwise addition of water. After acidification with 2N HCl, the mixture was extracted with diethyl ether (2×150 ml). The combined organic layers were dried over magnesium sulphate and the solvent was removed under vacuum to yield the desired alcohol (10.5 g) as an oil.

EXAMPLE 4

2,5-Di-O-allylbenzaldehyde

To a stirred solution of Collins reagent, made up from pyridine (44 g) and chromium trioxide (28.6 g) in dry dichloromethane (500 ml) at 0° C. was slowly added a solution of the benzyl alcohol (10.5 g) in dry dichloromethane (30 ml). After 30 minutes the solvent was removed under vacuum and replaced with diethyl ether (250 ml). The resulting suspension was filtered through celite and the residue was washed through with more diethyl ether. The combined organic fractions were washed with 2N HCl (50 ml), then dried over magnesium sulphate. Filtration and removal of solvent yielded the desired benzaldehyde (6.2 g) as a yellow oil.

EXAMPLE 5

2,5-Dihydroxy-3,6-diallylbenzaldehyde

The benzaldehyde (6.2 g) was heated, as a neat oil, at 180° C. for 3 hours under an atmosphere of nitrogen. The resulting rearranged product was recrystallised from cyclohexane to yield the desired compound as a yellow solid (4.1 g) (m.p. 102° C.).

EXAMPLE 6

Ethyl-5-[2,5-dihydroxy-3,6-diallylphenyl]pent-2E,4E-dieneoate

To a stirred solution of the stabilised ylid (8 g), preformed from the ethyl-5-bromo-crotanoate triphenyl phosphonium salt and sodium hydroxide, in toluene (100 g) was added the benzaldehyde (4 g). After 1 hour the solvent was removed under vacuum and replaced with a small quantity of dichloromethane. This crude product was purified by column chromatography, silica gel with dichloromethane elution, to yield the desired ethyl ester (2.9 g) as an orange oil.

The following compound was made by a similar method

Methyl-3-(2,5-dihydroxy-3,6-diallyphenyl-prop-2E-enoate.

EXAMPLE 7

Ethyl-5-[2,5-di-O-methylmethyl ether-3,6-diallylphenyl]pent-2E,4E-dieneoate

To a solution of the dihydroxy ester (1 g) in a two phase system of dichloromethane (20 ml) and aqueous sodium hydroxide (15%, 5 ml) containing a trace quantity of adogen 464 was added, dropwise, a solution of chloromethylmethyl ether (1.1 g). After 1 hour excess dichloromethane was added and the layers separated. The aqueous layer was extracted again with dichloromethane and the combined organic layers were dried over magnesium sulphate. Filtration and removal of solvent yielded the di-O-methylmethyl ether as an oil (0.9 g) after purification on a silica gel column with diethylether/hexane (1:1) elution.

EXAMPLE 8

5-[2,5-di-O-methylmethyl ether-3,6-diallylphenyl]pent-2,4-dieneoic acid

To a solution of the ethyl ester (0.9 g) in dimethoxy ethane (5 ml) and water (5 ml) was added an excess of lithium hydroxide. After 24 hours the solvents were removed under vacuum and the resulting solid was taken up in water (25 ml), acidified with 2N HCl, and extracted with ethyl acetate (3×20 ml). The combined organic layers were dried over magnesium sulphate. Filtration and removal of solvent yielded the desired acid (0.6 g).

EXAMPLE 9

1-[5-(2,5-di-O-methylmethyl ether-3,6-diallylphenyl)penta-2,4-dienoyl]piperidine To a solution of the acid (0.6 g) in dichloromethane was added oxalyl chloride (1.2 equivalents) and a catalytic amount of dimethylformamide. After 30 minutes the solvent was removed under vacuum and replaced with fresh dichloromethane. This solution of the acid chloride was added slowly to a solution of piperidine (0.30 g) in dichloromethane (10 ml), at 0° C. and under an atmosphere of nitrogen. After 2 hours the reaction was quenched with water and the organic layer separated and dried over magnesium sulphate. Filtration and removal of solvent yielded the desired amide (0.32 g) as an oil.

EXAMPLE 10

1-[5-(2,5-dihydroxy-3,6-diallylphenyl)penta-2,4-dienoyl]piperidine

The 2,5-di-O-methylmethyl ether derivative (0.3 g) was added to methanol which had been acidified with gaseous hydrogen chloride. The solution was stirred overnight when the solvent was removed under vacuum. The resulting oil was taken up in the diethyl ether (20 ml) and washed with water (2×10 ml). The combined organic layers were dried and the solvent removed to give the desired 2,5-dihydroxy derivative as an oil (0.2 g).

EXAMPLE 11

1-Carboxyethenyl-3-[2,5-dihydroxy-3,6-diallylphenyl]-morpholine

To a solution of the stabilised ylid, preformed from the 3-chloro ethenyl carboxy morpholine triphenyl phosphonium salt and sodium hydroxide in toluene was added 2,5-di-O-methylmethyl ether 3,6-diallylbenzaldehyde. The mixture was refluxed for 4 hours when the solvent was removed and the crude material purified by column chromatography, silica gel with diethyl ether elution, to yield the desired amide after deprotection of the hydroxyl groups.

EXAMPLE 12

2,5-Dihydroxy-3,6-diallylphenyl-alkenyl esters

To a solution of the phosphonium bromide, $Ph_3P^+CH_2(CH_2)_3CO_2EtBr^-$, (1.1 equivalent) in dry THF, at room temperature, and under an atmosphere of nitrogen was added $KO^tBu$ (1.2 equivalents) Immediately a red coloured solution formed and was stirred a further 15 minutes when a solution of 2,5-di-O-methylmethylether-3,6-diallyl benzaldehyde (1 equivalent) in dry tetrahydrofuran was added. The reaction mixture was stirred a further 4 hours then quenched with 2N HCl and extracted with diethylether. The resulting crude product was purified by column chromatography on silica gel using either dichloromethane or diethyl ethyl as eluting solvents.

The resulting olefins (E+Z isomers) were deprotected by stirring in a mixture of EtOH containing gaseous hydrogen chloride to give ethyl-(2,5-dihydroxy-3,6-diallylphenyl)hex-5-enoate.

The following compounds were prepared by a similar method:
Ethyl-12-(2,5-dihydroxy-3,6-diallylphenyl)dodec-11-enoate
Methyl-9-(2,5-dihydroxy-3,6-diallylphenyl)nona-5,8-dienoate Reduction with di-isobutyl aluminium hydride gave the following compound:
12-(2,5-Dihydroxy-3,6-diallylphenyl)dodec-11-en-1-ol.

Reduction by hydrogenation over 10% Pd/C gave:
Ethyl 6-(2,5-dihydroxy-3,6-dipropylphenyl)hexanoate.

EXAMPLE 13

2,5-Dihydroxy-3,6-diallylbenzaldehyde phenylhydrazine

A mixture of 2,5-diallyl-3,6-dihydroxy benzaldehyde (1.5 g), phenyl hydrazine (0.7 ml) and a catalytic amount of p-toluene sulphonic acid and toluene (150 mls) was refluxed under a Dean and Stark apparatus. The reaction was followed to completion using TLC. The toluene was removed under vacuum and the dark oil put down a silica-gel column with diethylether/hexane (1:1) elution. The product was further purified by recrystallisation from $CH_2Cl_2$/petroleum ether (40°-60° C.) to give a yellow solid, m.p. 79°-81° C.

The following compounds were similarly prepared:
2,5-Dihydroxy-3,6-diallylbenzaldehyde phenylhydrazone 79°-81° C.
2,5-Dihydroxy-3,6-diallybenzylidene acetylhydrazide 193°-194° C.
2,5-Dihydroxy-3,6-diallylbenzaldehyde-4-nitrophenylhydrazone 218°-220° C.

1-(2,5-Dihydroxy-3,6-diallylbenzylideneamino)morpholine 145°–146° C.
1-(2,5-Dihydroxy-3,6-diallylbenzylideneamino)piperidine
N-(2,5-Dihydroxy-3,6-diallylbenzylidene)-2-hydroxy-5-chloroaniline 108°–210° C.
6-(2,5-Dihydroxy-3,6-diallylbenzylideneamino)hexanoic acid
N-(2,5-Dihydroxy-3,6-diallylbenzylidene)dodecylamine 56° C.
N-(2,5-Dihydroxy-3,6-diallylbenzylidene)N,N-dimethyl-1,3-diaminopropane

EXAMPLE 14

2,5-Diallyl-3,6-dihydroxybenzaldoxime

Hydroxylamine hydrochloride (2 g) was dissolved in 20 ml of water and added to 2,5-diallyl-3,6-dihydroxybenzaldehyde (2 g). Enough ethanol was added to completely solubilise the aldehyde. The mixture was heated on a steam bath for ten minutes until TLC showed the reaction to be complete. The water and ethanol were evaporated and the solid recrystallised from ethanol/water, to give a beige solid, m.p. 241°–243° C.

EXAMPLE 15

3,6-Diallyl-2,5-dihydroxyphenyl-alkyl ketones (a) To the Grignard reagent, undecyl magnesium bromide, (1.1 equivalents) dry tetrahydrofuran (prepared from the halide and magnesium turnings) under nitrogen at room temperature was added a solution of 2,5-di-O-allyl benzaldehyde (1 equivalent) in dry tetrahydrofuran. After stirring for 4 hours the reaction was quenched with 2N HCl and extracted with diethyl ether. The crude product was purified by column chromatography using silica gel, with dichloromethane as the eluting solvent.

(b) To a solution of the aldehyde 2,5-di-O-allyl benzaldehyde (1 equivalent) in dry THF at room temperature and under an atmosphere of nitrogen was added methyl lithium (1.1 equivalent). After 2 hours the reaction was quenched with 2N HCl and extracted with diethylether. The crude product was purified as above.

(c) To a stirred suspension of Collins reagent (6 equivalents) in dry dichloromethane at 5° C. was slowly added the alcohol (1 equivalent). After 0.5 hours the solvent was removed under vacuum and replaced with diethyl ether. This suspension was then filtered through Celite and then washed with 2N HCl and dried over MgSO$_4$. Removal of the solvent left a crude material which was purified by column chromatography on silica gel with dichloromethane as the eluting solvent.

A neat solution of the O-allyl ketone was heated at 180°–200° C., under an atmosphere of nitrogen, for 2 hours. The product was allowed to cool and purified by column chromatography on silica gel using dichloromethane as the eluting solvent.

The following compounds were prepared by this method:
2,5-Dihydroxy-3,6-diallylphenyl undecyl ketone,
2,5-Dihydroxy-3,6-diallyl acetophenone.

EXAMPLE 16

N-(2,5-Dihydroxy-3,6-dipropylbenzyl) alkyl(aryl)amines

A solution of N-(2,5-dihydroxy-3,6-diallybenzylidene)-2-hydroxy-5-chloroaniline in dry tetrahydrofuran was hydrogenated over 10% Pd/C at room temperature and atmosphere pressure. After the required uptake of hydrogen had occurred the reaction mixture was filtered through Celite and the solvent removed under vacuum. The resulting amine, N-(2,5-dihydroxy-3,6-dipropylbenzyl)-2-hydroxy-5-chloroaniline, was recrystallised, m.p. 157°–159° C.

The following compound was similarly prepared:
N-(2,5-dihydroxy-3,6-dipropylbenzyl)ethanolamine.

The following Examples illustrate the preparation of typical formulations containing an active ingredient according to the invention.

EXAMPLE 17

Semi-Solid Matrix Capsule

Each capsule contains

| Active ingredient | 10 mg |
|---|---|
| PEG 4000 | 250 mg |

The PEG 4000 is melted and mixed with the active ingredient. Whilst still molten the mixture is filled into capsule shells and allowed to cool.

EXAMPLE 18

Tablet

Each tablet contains

| Active ingredient | 10 mg |
|---|---|
| Calcium carbonate | 300 mg |
| Magnesium stearate | 10 mg |
| Starch | 30 mg |
| Hydroxypropylmethylcellulose | 10 mg |
| Iron oxide | 4 mg |

The active ingredient is granulated with calcium carbonate and starch. The dried granulate is blended with lubricant and disintegrant and compressed into tablets of the required dosage strength. The tablet may then be coated.

EXAMPLE 19

Aerosol

| Active Ingredient | 10 mg |
|---|---|
| Ethanol | 90 mg |
| Propellant 11/12* | 900 mg |

The active ingredient is dissolved in ethanol and filled into a suitable pressurisable aerosol container. The container is filled with the propellant and sealed using conventional equipment.
The container may incorporate a metering valve.

*Proportions:
Propellant 11  30%
Propellant 12  70%

EXAMPLE 20

Hard Gelatin Capsule

Each capsule contains

| Active ingredient | 10 mg |
|---|---|
| Starch | 190 mg |

We claim:

1. A compound of the formula

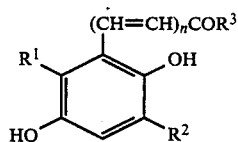

in which $R^1$ and $R^2$ are each $C_{3-7}$ alkyl or $R^{13}(CH=CHCH_2)_r$— where $R^{13}$ is hydrogen or $C_{1-8}$ alkyl and r is 1 to 3, and $R^3$ is —OH, —$OR^{14}$ where $R^{14}$ is $C_{1-4}$ alkyl or —$(CH_2)_2NR^{15}R^{16}$ where $R^{15}$ and $R^{16}$ are each hydrogen or $C_{1-4}$ alkyl, or —$NR^4R^5$ where $R^4$ and $R^5$ are each hydrogen, $C_{1-4}$ alkyl or phenyl optionally substituted by halogen or $C_{1-4}$ alkyl; and salts thereof.

2. A compound according to claim 1 in which $R^1$ and $R^2$ are both allyl or propyl, and $R^3$ is —OH or —$OR^{14}$ where $R^{14}$ is $C_{1-4}$ alkyl; and salts thereof.

3. The compound of claim 2 which is Ethyl-5-(2,5-dihydroxy-3,6-diallylphenyl)pent-2E,4E-dienoate.

4. A pharmaceutical formulation comprising a compound of the formula

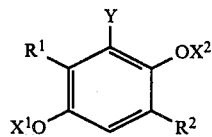

in which $R^1$ and $R^2$ are each hydrogen, $C_{1-12}$ alkyl or $C_{2-12}$ alkenyl, at least one of $R^1$ and $R^2$ being $C_{1-12}$ alkyl or $C_{2-12}$ alkenyl; $X^1$ and $X^2$ are each hydrogen; and Y is (a) —$(CH=CH)_nZ$ in which n is 1, 2 or 3 and Z is —CHO, —$CH_2OH$, —$COR^3$, —$(CH_2)_m$—$COR^3$ or —$(CH_2)_pCH=CH(CH_2)_q$—$COR^3$ in which m is an integer of 1 to 12, p is an integer of 1 to 4, q is an integer of 1 to 10 and $R^3$ is (i) —OH or (ii) —$NR^4R^5$ where $R^4$ and $R^5$ are each hydrogen, $C_{1-4}$ alkyl or optionally substituted phenyl, or $R^4$ and $R^5$ together with the nitrogen atom to which they are attached form a morpholino, pyrrolidinyl or piperidino ring, (b) —$CH=NR^6$ in which $R^6$ is (i) —OH, (ii) $C_{1-12}$ alkyl optionally substituted by —OH, —COOH or —$NR^7R^8$ where $R^7$ and $R^8$ are each hydrogen or $C_{1-4}$ alkyl, (iii) phenyl or substituted phenyl other than 2,4-dinitrophenyl or (iv) —$NR^9R^{10}$ in which $R^9$ is hydrogen and $R^{10}$ is optionally substituted phenyl or $C_{1-4}$ alkylCO—, or in which $R^9$ and $R^{10}$ together with the nitrogen atom to which they are attached form a morpholino, pyrrolidinyl or piperidino ring, or (c) —$CH_2NHR^{11}$ in which $R^{11}$ is $C_{1-12}$ alkyl optionally substituted with hydroxy or carboxy or optionally substituted phenyl;

provided that when one of $R^1$ and $R^2$ is hydrogen and the other is $C_{1-12}$ alkyl, Y is —$(CH=CH)_nZ$ and n is 1, Z is not —COOH or a pharmaceutically-acceptable salt thereof, in association with a pharmaceutically-acceptable diluent therefor.

5. A method of treating a mammal, including a human, suffering from an immediate hypersensitivity disease, which comprises administering to the mammal an effective amount of a compound of the formula

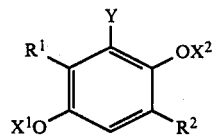

in which $R^1$ and $R^2$ are each hydrogen, $C_{1-12}$ alkyl or $C_{2-12}$ alkenyl, at least one of $R^1$ and $R^2$ being $C_{1-12}$ alkyl or $C_{2-12}$ alkenyl; $X^1$ and $X^2$ are each hydrogen; and Y is (a) —$(CH=CH)_nZ$ in which n is 1, 2 or 3 and Z is —CHO, —$CH_2OH$, —$COR^3$, —$(CH_2)_m$—$COR^3$ or —$(CH_2)_pCH=CH(CH_2)_q$—$COR^3$ in which m is an integer of 1 to 12, p is an integer of 1 to 4, q is an integer of 1 to 10 and $R^3$ is (i) —OH or (ii) —$NR^4R^5$ where $R^4$ and $R^5$ are each hydrogen, $C_{1-14}$ alkyl or optionally substituted phenyl, or $R^4$ and $R^5$ together with the nitrogen atom to which they are attached form a morpholino, pyrrolidinyl or piperidino ring, (b) —$CH=NR^6$ in which $R^6$ is (i) —OH, (ii) $C_{1-12}$ alkyl optionally substituted by —OH, —COOH or —$NR^7R^8$ where $R^7$ and $R^8$ are each hydrogen or $C_{1-4}$ alkyl, (iii) phenyl or substituted phenyl other than 2,4-dinitrophenyl or (iv) —$NR^9R^{10}$ in which $R^9$ is hydrogen and $R^{10}$ is optionally substituted phenyl or $C_{1-4}$ alkylCO—, or in which $R^9$ and $R^{10}$ together with the nitrogen atom to which they are attached form a morpholino, pyrrolidinyl or piperidino ring, or (c) —$CH_2NHR^{11}$ in which $R^{11}$ is $C_{1-12}$ alkyl optionally substituted with hydroxy or carboxy or optionally substituted phenyl;

provided that when one of $R^1$ and $R^2$ is hydrogen and the other is $C_{1-12}$ alkyl, Y is —$(CH=CH)_nZ$ and n is 1, Z is not —COOH; or a pharmaceutically-acceptable salt thereof.

* * * * *